United States Patent
Bennett

(10) Patent No.: US 8,766,004 B2
(45) Date of Patent: Jul. 1, 2014

(54) GREEN SYNTHESIS OF ARYL ALDIMINES USING ETHYL LACTATE

(75) Inventor: Jacqueline S. Bennett, Milford, NY (US)

(73) Assignee: The Research Foundation of State University of New York, Albany, NY (US)

( * ) Notice: Subject to any disclaimer, the term of this patent is extended or adjusted under 35 U.S.C. 154(b) by 653 days.

(21) Appl. No.: 13/006,162

(22) Filed: Jan. 13, 2011

(65) Prior Publication Data

US 2011/0196174 A1    Aug. 11, 2011

Related U.S. Application Data

(60) Provisional application No. 61/294,650, filed on Jan. 13, 2010.

(51) Int. Cl.
*C07C 249/02*    (2006.01)

(52) U.S. Cl.
USPC ............ 564/271; 564/272; 564/273; 564/248

(58) Field of Classification Search
CPC .................................................. C07C 249/02
USPC ........................................ 564/271, 272, 273
See application file for complete search history.

(56) References Cited

U.S. PATENT DOCUMENTS

| | | | |
|---|---|---|---|
| 7,713,955 B2 | 5/2010 | Whiteford et al. | |
| 8,067,402 B2 | 11/2011 | Whiteford et al. | |
| 8,067,403 B2 | 11/2011 | Whiteford et al. | |
| 8,153,617 B2 | 4/2012 | Whiteford | |
| 8,153,618 B2 | 4/2012 | Whiteford | |
| 8,188,068 B2 | 5/2012 | Whiteford | |
| 8,222,239 B2 | 7/2012 | Whiteford | |
| 8,268,381 B2 | 9/2012 | Whiteford et al. | |
| 2009/0054528 A1 | 2/2009 | Whiteford | |
| 2009/0069435 A1 | 3/2009 | Whiteford | |
| 2009/0074833 A1 | 3/2009 | Whiteford | |
| 2009/0105262 A1 | 4/2009 | Whiteford | |
| 2010/0004218 A1 | 1/2010 | Whiteford | |
| 2010/0016270 A1 | 1/2010 | Whiteford | |
| 2011/0015300 A1 | 1/2011 | Whiteford et al. | |
| 2013/0040924 A1 | 2/2013 | Whiteford | |
| 2013/0101516 A1 | 4/2013 | Zhao | |
| 2013/0150809 A1 | 6/2013 | Whiteford | |

FOREIGN PATENT DOCUMENTS

| | | |
|---|---|---|
| EP | 2125026 A2 | 12/2009 |
| WO | 2008/103847 A2 | 8/2008 |
| WO | 2010/019611 A2 | 2/2010 |
| WO | 2011/130114 A1 | 10/2011 |

OTHER PUBLICATIONS

Bennett et al., Green Chemistry, vol. 11, (2009), p. 166-168.*
Merlo et al. Molecular Crystals and Liquid Crystals Science and Technology, Section A: Molecular Crystals and Liquid Crystals (1998), 309, 111-116 (Abstract).*

* cited by examiner

*Primary Examiner* — Yong Chu
(74) *Attorney, Agent, or Firm* — Heslin Rothenberg Farley & Mesiti P.C.

(57) ABSTRACT

The present invention relates to a method for preparing aryl aldimines. In particular, the present invention relates to methods of preparing aryl aldimines that uses environmentally friendly solvent systems.

6 Claims, No Drawings

US 8,766,004 B2

GREEN SYNTHESIS OF ARYL ALDIMINES USING ETHYL LACTATE

CROSS REFERENCE TO RELATED APPLICATIONS

The present application claims priority to U.S. Provisional Application No. 61/294,650, filed Jan. 13, 2010, the entire contents of which are incorporated by reference herein.

FIELD OF THE INVENTION

The present invention relates to a method for preparing aryl aldimines. In particular, the present invention relates to methods of preparing aryl aldimines in a short time frame at room temperature that use environmentally friendly solvent systems, including green components such as ethyl lactate.

BACKGROUND OF THE INVENTION

Imines are important for a variety of applications. For example, imines are intermediates in many reactions of both enzymatic and pharmaceutical interest, making imines quite valuable and useful to a number of various fields. In particular, aryl aldimines are important for synthesis of a number of end products. Such end products include, for example, antibiotics and intermediates in the synthesis of antibiotics. From an environmental standpoint, aryl aldimines may be useful as additives to polymers to increase the rate of degradation of plastics in the environment.

Unfortunately, the formation of imines, such as aryl aldimines, has typically not involved environmentally friendly techniques and components. In addition, the methods used to make such imines are typically costly and involve lengthy reaction times. Traditional syntheses, for example, often involve the use of toxic solvents such as methylene chloride, and/or hazardous processes such as refluxing in petroleum-based solvents such as toluene as azeotroping agents. In one particular method, imines are made through reaction in toluene, which is a non-renewable solvent and is suspected to be teratogenic and mutagenic. Some recent imine syntheses have successfully used solvents or conditions that are more benign, but still require vigorous stirring, heat, recrystallization or other work up procedures, which negate some of the benefits of the green synthesis itself. Further, many of these processes result in a significant amount of waste, which again negates some of the benefits of green synthesis itself.

The present invention seeks to remedy these and other defects by providing a general method that is broadly applicable to a variety of imine syntheses, while also being environmentally friendly, efficient, and cost-sensitive.

SUMMARY OF THE INVENTION

In one aspect of the present invention, there is provided a method of preparing an imine including the use of a green solvent. The method may further include preparing an aldimine, and may include preparing an aryl aldimine. The method may include the steps of combining an amine and an aldehyde in the presence of a green solvent to form crystalline aldimines.

In another aspect there is provided a method of forming an imine including the use of a polarity-tuned solvent system. The polarity-tuned solvent may include a green solvent combined with a polar solvent, such as water, or another green solvent to achieve a desired polarity.

In another method, there is provided a method of determining the optimal polarity of a solvent in forming an aryl aldimine including the steps of: mixing an aryl amine and an aryl aldehyde in a pure solvent; determining the yield and purity of the resulting aryl aldimine; and modifying the polarity of the solvent so as to optimize the yield and purity of the resulting aryl aldimine.

DETAILED DESCRIPTION OF THE INVENTION

The present invention relates to the formation of imines. In one aspect of the invention, the methods described herein may be useful in the formation of aldimines, including but not limited to aryl aldimines. It will be understood by one of skill in the art that the present methods are not limited to aryl aldimines, however, and may be useful in preparing a variety of imines. In particular, the methods and products described herein are made in consideration of environmentally friendly ("green") principles. In some embodiments, the present methods may include the use of green solvents. In other embodiments, the present methods may include the use of green catalysts. In still other embodiments, the present methods may include the use of green processing methods, such as energy efficient methods and methods that reduce waste. Optimally, the methods described herein include combinations of green solvents, green catalysts, and green processing methods.

The present invention relates to a greener synthesis of imines, such as by using green solvents. As used herein, the term "green" refers to components and methods that are environmentally friendly. Environmentally friendly "green" chemistry seeks to include methods that reduce or eliminate waste products reduce or eliminate the use of toxic or hazardous solvents and procedures, avoid using energy-consuming methods, use renewable resources, increase energy efficiency, use components that are biodegradable and preferably minimize accident potential. Desirably, the components in the methods of the present invention, including the solvent, co-solvent and any other materials used to form the end product may have "green" features or attributes. Features of "green" compounds include, among others, the following: they may be approved by the FDA (or applicable governmental regulatory agency) as a food additive; may be derived from renewable resources; and may be biodegradable. Such characteristics of the components may help define just how environmentally friendly (or "green") the component is. A highly green material possesses each of the foregoing features, a moderately green material may include two of the features described above, and a slightly green material may include one of the features described above. It is preferable to use at least a moderately green material, and is more particularly desired to include a highly green material in the present invention.

Goals of the present invention include providing a method that requires little to no energy input, including energy in the form of stirring and/or heat, requires no recrystallization of product, or other purification methods after formation of the product. Although achievement of each goal is desired, it may be understood that achievement of one or more of the stated goals is acceptable.

In a preferred aspect, the solvent(s) chosen for the invention is renewable and biodegradable. The desired solvent may be miscible with water and nonpolar organic solvents. In some embodiments of the invention, ethyl lactate, such as ethyl L-lactate, may be used as the primary green solvent. Alternatively, ethyl acetate may be used. Although it has been discovered that ethyl acetate provides a pure material, it generally provides a lesser yield than ethyl lactate. Ethyl lactate is particularly desired because it demonstrates many of the desired "green" characteristics, including being approved by the FDA as a food additive, being derived from renewable resources, and being biodegradable, making it a highly green material.

A co-solvent may be added to the solvent of the system to "tune" the polarity of the system, allowing the end product to crystallize out of the composition as it is formed, while the starting materials remain dissolved. In some embodiments, water may be used as a polar co-solvent to increase solvent polarity and induce rapid formation of product. In some embodiments, methanol or ethanol may be used as a polar co-solvent, though less polar than water, to increase solvent polarity and induce rapid formation of product. In some embodiments, d-limonene, which can be extracted from citrus peel, may be used as a nonpolar co-solvent to decrease solvent polarity and induce rapid formation of product. Through the present methods described in further detail below, imines have been found to be crystallized directly out of solution in high purity and yield, requiring no further purification. The use of green solvents and green, environmentally efficient methods results in a more environmentally friendly process of forming the end products.

In one particular aspect of the invention, ethyl lactate is used as a solvent for forming the imine. Ethyl lactate is miscible with water as well as nonpolar organic solvents. Thus, a broad range of solvent polarity is accessible by simply "tuning" ethyl lactate with a cosolvent to create ideal conditions for rapid product formation. Thus, the present invention is capable of forming imines through the use of a solvent over a broad polarity range. Polarity adjustment may be made by using a co-solvent, such as water, other polar solvent, or a nonpolar solvent. Such adjustment may be used for optimizing crystallizations. The present invention is capable of producing imines under ambient conditions and processes so as to optimize reaction purity, yield, and speed. As used herein, the term "optimize" means to enhance effectiveness of the inventive process, and not necessarily refers to formation of an end product that is 100% pure or gives 100% yield. The term "optimize" simply refers to producing an end product with a higher level of purity, yield, and/or speed than traditional processes.

In some aspects, the present invention may use a solvent combined with 0% to about 40% (by volume) water or other polar solvent. The combination of the solvent with water or other solvent is useful in controlling the polarity of the solvent. Any common solvent may be used, including solvents that are very polar, such as water, and those solvents that are nonpolar, such as limonene. Thus, in one method, the invention includes adjusting the polarity of the solvent so as to efficiently prepare an imine. The present invention also provides a method of optimizing the polarity of the solvent through addition of co-solvents, such as water, to the green solvent used.

In other embodiments, the present invention involves preparing an imine through the use of less solvent volume than traditional methods for the same scale reaction. As used herein, the term "traditional methods" include methods that do not use green techniques, such as use of a green solvents or green methods described herein. For example, one "traditional method" includes formation of an imine through use of toluene as a solvent. In one aspect, the present invention provides a process of forming an imine by using about 10% of the solvent volume of traditional methods.

In another aspect, the present invention provides a process of preparing an imine in shorter time than is required in traditional methods. For example, the present invention may be capable of forming an imine in about 30 seconds to about 10 minutes at about room temperature. Desirably, the imine is formed in less than 10 minutes. A traditional method, for example, may require more than 2 hours of reaction time to form the desired imine. Other traditional methods are set forth in the Examples, and range in formation time from 2 hours to 24 hours.

Further, the present invention provides a process of preparing an imine without having to purify the imine after formation. Thus, desirably, after formation of the imine, the imine may be highly pure, such as at least 90% pure, at least 95% pure, or at least 99% pure. In preferred embodiments, the resulting imine is in excess of 98% pure. For example, the present invention may provide a process of forming an imine without the need to evaporate or boil off the solvent used to prepare the imine. The present invention may provide a process of forming an imine without the need to recrystallize the imine after formation. In addition, the present invention may provide a process of forming an imine without the need to use toxic solvents such as dichloromethane to purify the resulting product. For example, when ethyl lactate is used as the solvent, the solvent may be filtered through the resultant crystals. Remaining residue may be washed off with water and the crystals allowed to air dry. In this instance, there is no need to heat the solvent to be evaporated from the imine, which saves energy costs, waste disposal costs, and other costs incurred, which may be extremely high especially on a large-scale process.

As explained above, the present invention seeks to provide methods and processes for forming imines in environmentally friendly ways, such that the end product is useful and viable. In one aspect, the method results in an imine that does not require further purification. Further, in another aspect, the method provides a method of forming an imine that does not require additional heat during the processing steps. In yet another aspect, the present invention provides a method of forming an imine without the requirement for a separate catalyst.

Any imines may be formed through the present invention, including but not limited to aldimines. One particularly useful type of imines that may be formed include aryl aldimines, represented by the formula (1):

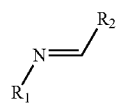

(1)

where $R_1$ and $R_2$ each include an aryl group. $R_1$ and $R_2$ may be the same or they may be different. The aryl groups useful herein include any desired aryl group, whether substituted or unsubstituted, and may include oxygens, nitrogens, halogens, or any other elements alone or in combination. Representative aryl groups include, but are not limited to the following structures: p-CH$_3$O—C$_6$H$_4$, p-NO$_2$—C$_6$H$_4$, p-CH$_3$—C$_6$H$_4$, p-Cl—C$_6$H$_4$, C$_6$H$_5$CH=CH, C$_6$H$_5$, o-HO—C$_6$H$_4$, p-Br—C$_6$H$_4$, p-F—C$_6$H$_4$, p-I—C$_6$H$_4$, p-HO—C$_6$H$_4$, 3,4-OCH$_2$O—C$_6$H$_3$, 4-HO-3-CH$_3$O—C$_6$H$_3$, 2-HO-3-CH$_3$—O—C$_6$H$_3$, p-CH$_3$CH$_2$O—C$_6$H$_4$, p-CH$_3$CH$_2$—C$_6$H$_4$, p-BnO—C$_6$H$_4$, p-PhO—C$_6$H$_4$, p-Me$_2$N—C$_6$H$_4$, p-Me$_2$CH—C$_6$H$_4$, and combinations thereof.

Aryl aldimines that may be formed through the present inventive methods include but are not limited to salicylidene-anilines (which are active against tuberculosis), cinnamylidene imines (which are useful as intermediates in preparation of beta-lactam antibacterial compounds and which accelerate photodegradation of polyethylene), p-hydroxybenzylideneanilines (which are useful as intermediates in preparation of cholesterol-lowering drugs, such as Zetia, or acrylate monomers used to make various acrylate-based polymers).

One typical process of forming the imine is now described. This process may be used to form any desired imine, including but not limited to aldimines such as aryl aldimines. In a first step, a primary amine may be provided. Any desired primary amine or amines may be provided, depending upon the desired resulting imine. For example, when an aryl aldimine is desired, the amine may include an aryl amine represented by the structure below (2):

$$R\text{—}NH_2 \qquad (2)$$

where R includes any aryl group. The aryl groups useful herein include any desired aryl group, whether substituted or unsubstituted, and may include oxygens, nitrogens, halogens, or any other elements alone or in combination. Representative aryl groups include, but are not limited to the following structures: p-CH$_3$O—C$_6$H$_4$, p-NO$_2$—C$_6$H$_4$, p-CH$_3$—C$_6$H$_4$, p-Cl—C$_6$H$_4$, C$_6$H$_5$CH=CH, C$_6$H$_5$, o-HO—C$_6$H$_4$, p-Br—C$_6$H$_4$, p-F—C$_6$H$_4$, p-HO—C$_6$H$_4$, 3,4-OCH$_2$O—C$_6$H$_3$, 4-HO-3-CH$_3$O—C$_6$H$_3$, and combinations thereof. One particularly useful aryl amine is aniline.

The amount of starting amine will depend upon the amount of resulting imine desired. For example, on a small scale batch, anywhere from about 1 to about 100 mmol of the starting amine may be used. Larger amounts of starting materials will result in larger amounts of imines.

The starting amine may then be dissolved in the chosen solvent. As explained above, any solvent may be selected, and desirably the solvent is a green solvent. The solvent may be polarity-tuned by a cosolvent, if desired. In one particularly useful embodiment, the solvent may be ethyl lactate (such as ethyl L-lactate), and a polar cosolvent may be water. The resulting mixed solvent may have any desired polarity. The mixed solvent may include about 0 to about 40% of the polar solvent by weight of the mixed solvent, and more particularly may include about 5% polar solvent, 10% polar solvent, about 15% polar solvent, about 20% polar solvent, about 25% polar solvent, about 30% polar solvent, about 35% polar solvent or about 40% polar solvent by volume of the mixed solvent. For example, the mixed solvent may include 80% ethyl lactate and 20% water by volume of the mixed solvent. Desirably, the amount of the mixed solvent is sufficient to drive the reaction forward. It may be desired to tune the polarity of the solvent mixture by adding more co-solvent until the desired level is reached.

In the case of formation of an aryl aldimine, for example, after the starting amine is dissolved in the mixed solvent, an aldehyde (which may also be predissolved in the mixed solvent) may be added to the amine mixture. The aldehyde selected will depend upon the desired resulting imine. Desirably the amount of aldehyde should be approximately equimolar to the amount of starting imine used to avoid purification to remove the component in excess following reaction. However, slight variations may be acceptable.

For example, if the desired resulting imine is cinnamylidine aniline, the starting amine is desirably aniline and the starting aldehyde is desirably cinnamaldehyde.

This reaction mixture may be swirled until approximately homogenous and then allowed to sit undisturbed for the desired length of time. The reaction time may be from about 10 seconds to about 10 minutes, if desired. It is preferred that the initial swirling time be lower than the time to be sit undisturbed, and most desirably is about 2-5 seconds. The length of time that the mixture is allowed to sit undisturbed may be any time from about 30 seconds to about 20 minutes, and more particularly about 1 to about 10 minutes or from about 1 to about 5 minutes. Most desirably, the time to sit undisturbed is less than 10 minutes. The swirling and sitting stages are desirably performed at about room temperature. During the time that the reaction mixture is allowed to sit undisturbed, imine crystals will form. In some embodiments, it may be useful to slightly chill the mixture after it has been allowed to sit at room temperature for the desired length of time. For example, the mixture may be chilled in an ice bath at about 0° C. for less than five minutes.

When crystallization is complete (i.e., at the end of the time period allowed to sit undisturbed), the crystals may be harvested. Any desired harvesting may be used, so as to gather the resulting crystals. In one embodiment, crystals may be chilled on ice. Another aspect of harvesting includes rinsing the crystals with a rinsing agent, such as brine and/or water. The crystals may be vacuum filtered if desired. Crystals may be allowed to air dry. For example, crystals may be chilled, rinsed with brine and vacuum filtered, then washed with cold water and allowed to air dry. It may be necessary to desiccate the resulting crystals to fully remove water, particularly when humidity levels are high and the imine contains a hygroscopic moiety, such as a hydroxy group.

The resulting crystalline imine is desirably highly pure and thus avoids the need for recrystallization. Therefore, there is no need to take steps to further purify the resulting imine. After the resulting imine is formed, it may be used as a starting material for one of any number of final compounds, including, for example, antibiotics, cholesterol-lowering drugs, or acrylate monomers used to make various acrylate-based polymers. Thus, in some embodiments, the present invention provides methods of forming such final compounds using energy efficient, green methods described above.

The present invention further provides an imine formed by the processes described above. The imine is desirably formed with attention to green principles, such as using green starting materials, green catalysts, energy efficient methods, waste reduction methods, and the like.

The present invention additionally provides a method of determining the optimal polarity of a solvent in forming an aryl aldimine. In this method, an aryl amine and an aryl aldehyde are first mixed in a green solvent that has not been tuned with a co-solvent. The aryl aldimine is formed. The yield of the resulting aryl aldimine is determined after a desired time, for example, after 10 minutes. Determining the yield after the desired run time allows the user to determine whether the yield is sufficiently high. If it is not as high as desired (i.e., at least 95%, for example), the user may then modify the polarity of the solvent. Modifying the polarity of the solvent includes, for example, adding incremental amounts of a co-solvent, such as water, to the solvent. The modified polarity solvent is then used to form the aryl aldimine, and the yield of aryl aldimine is determined. If the yield is not as high as desired (for example, at least 95%), the user may modify the polarity of the solvent yet again. This process is repeated until the yield of the aryl aldimine is as high as desired. Any of the solvents described above may be used in this method, including green solvents, such as ethyl lactate. In addition, the co-solvent may be any polar or non-polar solvent desired, such as water. Any level of co-solvent in the mixture may be useful in the "optimal" polarity, and in some embodiments, the co-solvent is present in an amount of from about 0% to about 40% by weight of the solvent combination.

The methods described above may be useful in the formation of other imines. For example, it may be desirable to tune in the green solvent n the nonpolar direction, such as using d-limonene/ethyl lactate, and reacting with p-phenylbenzaldehyde. Thus, the invention may be used to form, for example, benzylamine-derived imines or aryl ketimines, and still use "green" components and be performed in environmentally friendly methods.

The present invention may be more fully understood through the non-limiting Examples set forth below, which are illustrative of the invention.

EXAMPLES

Example 1

Formulation of Aryl Aldimines Using Ethyl Lactate

A variety of aryl aldimines were synthesized pursuant to the processes of the present invention. In particular, imines were to be synthesized with attention to the desired "green" principles described above, including for example, use of biodegradable materials, use of materials derived from renewable resources, avoiding the need for purification methods, using energy efficient methods, and reducing waste. In this Example, ethyl lactate (EL) was used as the solvent, either by itself or mixed with water. The polarity of the ethyl lactate was tuned with water. To demonstrate the versatility of this solvent tuning technique for generating aryl aldimines, a variety of aryl aldehydes and aryl amines containing both activating and deactivating substituents were examined. The results are set forth in Table 1 below.

The aryl aldimines were prepared by combining a solvent, an aryl amine and an aryl aldehyde (having aryl groups as set forth in Table 1 below), mixing until homogenous, and allowing the resulting mixtures to sit undisturbed. The solvent used was ethyl lactate in combination with water. The percentage of ethyl lactate used varied from 70% to 100%, depending upon the imine synthesized. The process was completed at approximately ambient temperature. The time was measured from when the amine and aldehyde were combined to the end of crystallization.

Table 1 below sets forth the run, the substituents generated, the time to generate the imine, the yield of the imine and a measure of purity (measured by the resultant melting point). The Table below lists published data obtained from literature for comparison between the resultant imine and known imines. Comparative data obtained from published literature relating to known properties of the imine is depicted in parentheses in Table 1. All melting points, including those obtained from literature, are uncorrected. Literature melting points are generally acquired from recrystallized imines, whereas melting points prepared from the present invention were acquired from unrecrystallized imines. Full spectroscopic characterization of products was generated for further analysis.

All reactions were first run in pure ethyl L-lactate. Reactions that took more than ten minutes were tuned with water to reduce reaction time. The % EL values in Table 1 reflect the mixture used to generate a high quality crystal with a fast reaction speed. While the mechanistic aspects of this reaction were not examined, the present applicants surmise water exerted its effect by one or both of the following routes: (1) water stabilized the carbinolamine intermediate, which accelerated the reaction or (2) the obvious crystallization of the imine product made it apparent when the reaction was complete, thus, excess time was not wasted to ensure reaction completion.

TABLE 1

Aryl Aldimines Synthesized Using Ethyl Lactate

| Run | Solvent (% EL) | R1 | R2 | Time | mp | % Yield |
|---|---|---|---|---|---|---|
| a | 100 | p-CH$_3$O—C$_6$H$_4$ | p-NO$_2$—C$_6$H$_4$ | 1-3 min (24 h, Δ) | 133-134 (134) | 94 (100) |
| b | 100 | p-CH$_3$O—C$_6$H$_4$ | p-Cl—C$_6$H$_4$ | 0.5-1 min (6 h) | 127-129 (124-125) | 93 (100) |
| c | 95 | p-CH$_3$O—C$_6$H$_4$ | C$_6$H$_5$CH=CH | 0.5-1.5 min (2 h) | 119-120 (116-119) | 96 (88) |
| d | 90 | p-CH$_3$O—C$_6$H$_4$ | p-CH$_3$O—C$_6$H$_4$ | 1-3 min (5-10 min) (nr) | 144 (nr) (142) | 93 (>99) (nr) |
| e | 100 | p-CH$_3$—C$_6$H$_4$ | p-Cl—C$_6$H$_4$ | 1-2 min (6 h) | 124-125 (125) | 96 (100) |
| f | 100 | p-CH$_3$—C$_6$H$_4$ | p-HO—C$_6$H$_4$ | 1-2 min (2 h) | 217-220 (215) | 90 (100) |
| g | 80 | p-CH$_3$—C$_6$H$_4$ | o-HO—C$_6$H$_4$ | 2-4 min (>10 min) | 94 (95-96) | 97 (90) |
| h | 90 | Ph | p-Cl—C$_6$H$_4$ | 4-6 min (2 h) | 63-64 (58-61) | 95 (97) |
| i | 90 | Ph | p-Br—C$_6$H$_4$ | 3-5 min (1 h) | 71-72 (71-74) | 99 (86) |
| j | 80 | Ph | C$_6$H$_5$CH=CH | 2-4 min (5-10 min) (10-30 min) (nr) | 108-109 (nr) (nr) (109) | 98 (85) (89) (nr) |
| k | 90 | Ph | p-HO—C$_6$H$_4$ | 5-7 min (30 min) (3 min) | 193-194 (50-53) (195) | >99 (94) (95) |
| l | 100 | p-Br—C$_6$H$_4$ | p-Cl—C$_6$H$_4$ | 1-2 min | 119-120 | 96 |
| m | 70 | p-Br—C$_6$H$_4$ | Ph | 3-5 min (30 min) | 66-68 (62-65) | 93 (98) |
| n | 80 | p-Br—C$_6$H$_4$ | o-HO—C$_6$H$_4$ | 2-3 min | 111 (nr) | 96 (nr) |

TABLE 1-continued

Aryl Aldimines Synthesized Using Ethyl Lactate

| Run | Solvent (% EL) | R1 | R2 | Time | mp | % Yield |
|---|---|---|---|---|---|---|
| o | 80 | p-Cl—$C_6H_4$ | p-Cl—$C_6H_4$ | 2-3 min (30 min) | 110-111 (110-113) | 97 (87) |
| p | 80 | p-Cl—$C_6H_4$ | $C_6H_5CH=CH$ | 1-2 min | 105 | 97 |
| q | 90 | p-Cl—$C_6H_4$ | o-HO—$C_6H_4$ | 6-10 min (nr) | 104 (101-102) | 96 (nr) |

Through the inventive processes described above, the Applicants found no need for catalysts to drive the imine synthesis. Even further, the Applicants found no need for external energy for most of the reactions, including heat. In addition, the Applicants found that the yield achieved was typically as high, if not higher, than reported yields through formation of the imine through traditional methods. The resulting products were found to be substantially pure, as measured by reported melting point and confirmed by spectroscopic characterization.

Perhaps most surprisingly, it was found that the time to form the resulting imine, as measured from start to crystallization, was substantially reduced as compared to reported formation times. In some instances, the time for formation of the imine may be reduced to less than about 5% to about 10% of the reported time to traditionally form the imine, and in some instances, the time may be reduced to less than about 1% of the reported time to traditionally form the imine.

Only one example (run a) required heat due to solubility problems with the p-nitrobenzaldehyde, but the reaction was complete within three minutes, compared to 24 h of continuous heat in the literature method. Even this method, which uses added heat, would be more environmentally conscious than the comparative method, given the significant time reduction in forming the material.

Example 2

Formulation of Additional Aryl Aldimines Using Ethyl Lactate

Subsequent testing was conducted to develop further aryl aldimines, as set forth in Table 2 below. The imines were prepared using the same process described in Example 1.

TABLE 2

Additional Aryl Aldimines Synthesized Using Ethyl Lactate

| | Solvent (% EL) | R1 | R2 | Time | mp ° C. | % Yield |
|---|---|---|---|---|---|---|
| 1 | 80 | p-$CH_3O$—$C_6H_4$ | $C_6H_5$ | ~5 min | 62-64 | 94% |
| 2 | 100 | p-$CH_3O$—$C_6H_4$ | p-F—$C_6H_4$ | 1-3 min | 93.5-95.5 | 93% |
| 3 | 80 | p-$CH_3O$—$C_6H_4$ | p-HO—$C_6H_4$ | 1-3 min | 210-211 | >99% |
| 4 | 80 | p-$CH_3O$—$C_6H_4$ | 3,4-$OCH_2O$—$C_6H_3$ | 2-5 min | 111-112 | >99% |
| 5 | 80 | p-$CH_3O$—$C_6H_4$ | 4-HO-3-$CH_3O$—$C_6H_3$ | 9-22 min | 132-133 | 93% |
| 6 | 90 | p-$CH_3$—$C_6H_4$ | p-F—$C_6H_4$ | 3-5 min | 61-63 | 94% |
| 7 | 100 | p-$CH_3$—$C_6H_4$ | p-Br—$C_6H_4$ | 32-37 min | 137.5-139.5 | 95% |
| 8 | 90 (10 ml) | p-$CH_3$—$C_6H_4$ | p-HO—$C_6H_4$ | 1-3 min | 219-220 | 94% |
| 9 | 80 | p-$CH_3$—$C_6H_4$ | p-$CH_3O$—$C_6H_4$ | 3-5 min | 92.5-93.5 | 93% |
| 10 | 80 | p-$CH_3$—$C_6H_4$ | $C_6H_5CH=CH$ | 3-10 min | 79-80 | 97% |
| 11 | 100 (3 mL) | p-Br—$C_6H_4$ | p-F—$C_6H_4$ | 17-25 min | 50-51 | 94% |
| 12 | 100 | p-Br—$C_6H_4$ | p-Br—$C_6H_4$ | 1-2 min | 139-140 | 96% |
| 13 | 90 | p-Br—$C_6H_4$ | $C_6H_5CH=CH$ | <1 min | 118-119 | 95% |
| 14 | 80 | p-Br—$C_6H_4$ | 3,4-$OCH_2O$—$C_6H_3$ | 3-6 min | 107-108 | 96% |
| 15 | 90 (4 mL) | p-Cl—$C_6H_4$ | p-F—$C_6H_4$ | 5-9 min (ice) | 71-72 | 91% |
| 16 | 100 | p-Cl—$C_6H_4$ | p-Br—$C_6H_4$ | 2-4 min | 120-121 | 93% |
| 17 | 100 (10 mL) | p-Cl—$C_6H_4$ | p-$NO_2$—$C_6H_4$ | <13 min | 130-131 | >99% |
| 18 | 80 | p-Cl—$C_6H_4$ | p-HO—$C_6H_4$ | 3-5 min | 185-187 | 94% |
| 19 | 80 | p-Cl—$C_6H_4$ | p-$CH_3O$—$C_6H_4$ | 3-5 min | 90-92 | 96% |
| 20 | 100 | p-Cl—$C_6H_4$ | 3,4-$OCH_2O$—$C_6H_3$ | 25-37 min | 86-87 | 94% |
| 21 | 70 | p-Cl—$C_6H_4$ | 4-HO-3-$CH_3O$—$C_6H_3$ | 30-60 min | 125-126 | 94% |
| 22 | 100 | p-Br—$C_6H_4$ | p-$CH_3$—$C_6H_4$ | 2 min | 131-132 | 86 |
| 23 | 80 | p-Br—$C_6H_4$ | p-$CH_3O$—$C_6H_4$ | 6 min | 119-120 | 99 |
| 24 | 80 | p-Br—$C_6H_4$ | p-HO—$C_6H_4$ | 5 min | 194 | 88 |
| 25 | 100 | p-Cl—$C_6H_4$ | p-$CH_3$—$C_6H_4$ | 2 min | 117-118 | 82 |
| 26 | 80 | p-$Me_2N$—$C_6H_4$ | $C_6H_5$—CH=CH | 9 sec | 145-147 | 99 |
| 27 | 80 | p-$Me_2N$—$C_6H_4$ | o-HO—$C_6H_4$ | 17 sec | 138-139 | 99 |
| 28 | 90 | p-$CH_3CH_2O$—$C_6H_4$ | 2-HO-3-MeO—$C_6H_3$ | 5 min | 96-97 | 98 |
| 29 | 90 | p-$CH_3CH_2O$—$C_6H_4$ | $C_6H_5$—CH=CH | <1 min | 109 | 95 |
| 30 | 90 | p-$CH_3CH_2O$—$C_6H_4$ | m-Cl—$C_6H_4$ | 17 min | 66-67 | 90 |
| 31 | 90 | p-$CH_3CH_2O$—$C_6H_4$ | p-Br—$C_6H_4$ | 4 min | 134-135 | 96 |
| 32 | 90 | p-$CH_3CH_2O$—$C_6H_4$ | p-Cl—$C_6H_4$ | <1 min | 122-123 | 96 |
| 33 | 80 | p-$CH_3CH_2O$—$C_6H_4$ | $C_6H_5$ | 5 min | 71 | 84 |

TABLE 2-continued

Additional Aryl Aldimines Synthesized Using Ethyl Lactate

| | Solvent (% EL) | R1 | R2 | Time | mp °C. | % Yield |
|---|---|---|---|---|---|---|
| 34 | 90 | p-$CH_3CH_2O$—$C_6H_4$ | p-$CH_3$—$C_6H_4$ | <1 min | 108-109 | 89 |
| 35 | 90 | p-$CH_3CH_2O$—$C_6H_4$ | p-$CH_3O$—$C_6H_4$ | 3 min | 130-131 | 93 |
| 36 | 90 (26 mL) | p-$CH_3CH_2O$—$C_6H_4$ | p-$NO_2$—$C_6H_4$ | 4 min | 125-126 | 94 |
| 37 | 90 | p-$CH_3CH_2O$—$C_6H_4$ | p-HO—$C_6H_4$ | 6 min | 204-205 | 90 |
| 38 | 90 | p-$CH_3CH_2O$—$C_6H_4$ | o-HO—$C_6H_4$ | 9 min | 93-94 | 95 |
| 39 | 90 | p-$CH_3CH_2$—$C_6H_4$ | p-Br—$C_6H_4$ | 2 min | 103-104 | 98 |
| 40 | 90 | p-$CH_3CH_2$—$C_6H_4$ | p-Cl—$C_6H_4$ | 2 min | 103-104 | 95 |
| 41 | 90 | p-$CH_3CH_2$—$C_6H_4$ | p-HO—$C_6H_4$ | 8 min | 200-201 | 88 |
| 42 | 90 | p-F—$C_6H_4$ | 2-HO-3-MeO—$C_6H_3$ | 6 min | 97-98 | 89 |
| 43 | 100 | p-F—$C_6H_4$ | $C_6H_5$—$CH_2$ | 8 min | 135-136 | 98 |
| 44 | 80 | p-F—$C_6H_4$ | p-F—$C_6H_4$ | 4 min | 64-65 | 95 |
| 45 | 90 | p-F—$C_6H_4$ | p-$CH_3$—$C_6H_4$ | 7 min | 65-66 | 83 |
| 46 | 80 | p-F—$C_6H_4$ | p-$CH_3O$—$C_6H_4$ | 9 min | 66-67 | 85 |
| 47 | 80 | p-F—$C_6H_4$ | p-$NO_2$—$C_6H_4$ | 20 min | 109-111 | 87 |
| 48 | 80 | p-F—$C_6H_4$ | p-HO—$C_6H_4$ | 2 min | 182 | 91 |
| 49 | 80 | $C_6H_5$ | p-$CH_3O$—$C_6H_4$ | 22 min | 60 | 85 |
| 50 | 100 | p-I—$C_6H_4$ | $C_6H_5$—CH=CH | 2 min | 135-136 | 93 |
| 51 | 100 | p-I—$C_6H_4$ | p-Br—$C_6H_4$ | 2 min | 173-175 | 90 |
| 52 | 100 | p-I—$C_6H_4$ | p-Cl—$C_6H_4$ | 2 min | 140-141 | 98 |
| 53 | 80 | p-I—$C_6H_4$ | p-F—$C_6H_4$ | 2 min | 88 | 96 |
| 54 | 80 | p-I—$C_6H_4$ | p-$Me_2$CH—$C_6H_4$ | 3 min | 88-89 | 92 |
| 55 | 100 | p-I—$C_6H_4$ | p-$CH_3O$—$C_6H_4$ | 10 min | 153-154 | 99 |
| 56 | 100 | p-I—$C_6H_4$ | o-HO—$C_6H_4$ | 20 min | 131-132 | 94 |
| 57 | 100 | p-$Me_2$CH—$C_6H_4$ | p-Cl—$C_6H_4$ | 2 min | 103-104 | 95 |
| 58 | 80 | p-$Me_2$CH—$C_6H_4$ | p-F—$C_6H_4$ | 3 min | 79-80 | 98 |
| 59 | 90 | p-$CH_3O$—$C_6H_4$ | m-Cl—$C_6H_4$ | 4 min | 71-73 | 94 |
| 60 | 90 | p-$CH_3O$—$C_6H_4$ | o-Cl—$C_6H_4$ | 31 min | 62-64 | 86 |
| 61 | 90 | p-$CH_3O$—$C_6H_4$ | p-$CH_3$—$C_6H_4$ | 2 min | 85-86 | 88 |
| 62 | 90 | p-$CH_3O$—$C_6H_4$ | o-HO—$C_6H_4$ | 5 min | 85 | 96 |
| 63 | 80 | p-$CH_3O$—$C_6H_4$ | 4-HO-3-$CH_3O$—$C_6H_3$ | 30 min | 132-133 | 93 |
| 64 | 80 (26 mL) | p-$CH_3$—$C_6H_4$ | p-$NO_2$—$C_6H_4$ | 2 min | 120-121 | 99 |
| 65 | 100 | p-PhO—$C_6H_4$ | $C_6H_5$—CH=CH | 4 min | 100 | 99 |
| 66 | 100 | p-PhO—$C_6H_4$ | p-Br—$C_6H_4$ | 4 min | 128-129 | 97 |
| 67 | 80 | p-PhO—$C_6H_4$ | p-$Me_2$CH—$C_6H_4$ | 11 min | 49-52 | 98 |
| 68 | 100 | p-PhO—$C_6H_4$ | p-$CH_3$—$C_6H_4$ | 8 min | 79-80 | 95 |
| 69 | 100 | p-PhO—$C_6H_4$ | p-$CH_3O$—$C_6H_4$ | 5 min | 114-115 | 96 |
| 70 | 100 | p-PhO—$C_6H_4$ | p-HO—$C_6H_4$ | 2 min | 204 | 54 |

Again, as can be seen, the time to form the imine through the present invention was generally on the order of minutes, in most instances taking less than 10 minutes to form the imine. The percentage yield and the purity (as determined using $^1$H NMR) through the inventive methods described herein were consistently in the mid- to high-90%, demonstrating efficient formation. Thus, a high yield of sufficiently pure material was formed in a sufficiently short time frame (i.e., within about 10 minutes). This demonstrates formation using green methods.

Example 3

Comparison of Published Results to Invention

Four published combinations were considered and prepared using the inventive "green" methods described herein. The inventive methods were performed using ethyl L-lactate (EL) and water having ethyl L-lactate levels of from 100% to 70%. The published combinations were formed through use of the stated materials and time/energy required, and each required recrystallization. The inventive method did not require recrystallization. The results are set forth in Table 3 below.

TABLE 3 comparisons of published combinations to inventive combinations

| | Published Results | | Inventive Results | |
|---|---|---|---|---|
| | | | Time; | |
| Combination | Time, auxiliary parameters | Yield and m.p. | EL amount in solvent | Yield and m.p. |
| cinnamaldehyde + aniline (Guzen) | 5-10 min sonication; EtOH; silica; dichloromethane purification | >85%, m.p. not reported (109° C.) | 3 min; 80% EL | 98%; m.p. 108-109° C. |

TABLE 3-continued comparisons of published combinations to inventive combinations

| | Published Results | | | Inventive Results | |
|---|---|---|---|---|---|
| Combination | Time, auxiliary parameters | Yield and m.p. | Time; EL amount in solvent | Yield and m.p. | |
| p-chloro-benzaldehyde + p-anisidine (Schmeyers) | Thorough grinding required; room temperature for 6 hours; vacuum removal of water at 80° C. | 100%; m.p. 124-125° C. | 1 min; 100% EL | >93%; m.p. 127-129° C. | |
| p-nitro-benzaldehyde + p-anisidine (Schmeyers) | Thorough grinding required; heat 24 hours; vacuum removal of water at 80° C. | 100%; m.p. 134° C. | 3 min; 100% EL | 94%; m.p. 133-134° C. | |
| p-bromoaniline + benzaldehyde (Tanaka) | 1 hour room temperature with stirring | 98%; m.p. 62-65° C. | 5 min; 70% EL | 93%; m.p. 66-68° C. | |

As can be seen, the inventive green methods resulted in highly pure resulting materials, high yield, and required significantly less time and energy as that of the published methods. The inventive methods are sufficiently "green" as desired.

Example 4

Formulation of Cinnamylidene Aniline

Cinnamylidine was prepared as explained below. The result of the synthesis of cinnamylidine aniline is depicted as run (j) in Table 1 of Example 1.

10 mmol aniline was dissolved in approximately 2.5 mL 80% ethyl L-lactate in water (v/v). Separately, 10 mmol of cinnamaldehyde was dissolved in approximately 2.5 mL 80% ethyl L-lactate in water (v/v). The two solutions were combined and the resulting reaction mixture was swirled until homogeneous and then allowed to sit undisturbed at room temperature for four minutes, when crystal formation was complete. Crystals were chilled, rinsed with cold brine and vacuum filtered, washed with cold water, and allowed to air dry. Some of the hydroxyl-containing imines had to be desiccated to completely remove water, especially when humidity was high. All melting points and spectroscopic data were acquired on the crude imines. However, these imines can be recrystallized from ethyl lactate or low molecular weight alcohols.

Various changes and modifications may be made in the present invention. It is intended that all such changes and modifications come within the scope of the invention as set forth in previous discussion.

What is claimed is:

1. A method of forming an aryl aldimine comprising the steps of:
   a. mixing an aryl amine and an aryl aldehyde in a solvent comprising ethyl lactate;
   b. determining the yield of the resulting aryl aldimine; and
   c. modifying the polarity of the solvent so as to optimize the yield of the resulting aryl aldimine.

2. The method of claim 1, wherein the solvent further comprises water and wherein said step of modifying the polarity of the solvent comprises mixing said ethyl lactate and water to achieve a desired polarity level.

3. The method of claim 2, wherein said water is added in an amount up to about 40% by weight of said solvent mixture.

4. The method of claim 1, wherein said aryl aldimine is formed at room temperature.

5. The method of claim 1, comprising purifying said aryl aldimine without recrystallization.

6. The method of claim 1, comprising purifying said aryl aldimine without evaporating remaining solvent.

* * * * *